United States Patent
Patnaik et al.

(10) Patent No.: US 10,239,830 B2
(45) Date of Patent: Mar. 26, 2019

(54) BENZENESULFONAMIDE UPREGULATORS OF NPC1 FOR NEIMANN-PICK DISEASE AND OTHER LYSOSOMAL STORAGE DISORDERS

(71) Applicants: ICAHN SCHOOL OF MEDICINE AT MOUNT SINAI, New York, NY (US); The United States of America, as represented by the Secretary, Department of Health and Human Services, Washington, DC (US)

(72) Inventors: Samarjit Patnaik, Rockville, MD (US); Mercedes Taylor, Berkeley, CA (US); Raul Rolando Calvo, Rockville, MD (US); Juan Jose Marugan, Rockville, MD (US); Noel Southall, Rockville, MD (US); Wei Zheng, Rockville, MD (US); Marc Ferrer-Alegre, Rockville, MD (US); Seameen Dehdasthi, Rockville, MD (US); Patricia Dranchak, Rockville, MD (US); Fannie Chen, New York, NY (US); Yiannis Ioannou, New York, NY (US)

(73) Assignees: ICAHN SCHOOL OF MEDICINE AT MOUNT SINAI, New York, NY (US); The United States of America, as represented by the Secretary, Depart. of Health and Human Services, Washington, DC (US)

(*) Notice: Subject to any disclaimer, the term of this patent is extended or adjusted under 35 U.S.C. 154(b) by 0 days.

(21) Appl. No.: 15/549,743

(22) PCT Filed: Feb. 11, 2016

(86) PCT No.: PCT/US2016/017504
§ 371 (c)(1),
(2) Date: Aug. 9, 2017

(87) PCT Pub. No.: WO2016/130774
PCT Pub. Date: Aug. 18, 2016

(65) Prior Publication Data
US 2018/0044286 A1 Feb. 15, 2018

Related U.S. Application Data

(60) Provisional application No. 62/114,840, filed on Feb. 11, 2015.

(51) Int. Cl.
C07C 311/21 (2006.01)
A61K 31/4164 (2006.01)
A61K 31/44 (2006.01)
C07D 207/335 (2006.01)
C07D 213/46 (2006.01)
C07D 233/64 (2006.01)
A61K 31/165 (2006.01)

(52) U.S. Cl.
CPC .......... *C07C 311/21* (2013.01); *A61K 31/165* (2013.01); *A61K 31/4164* (2013.01); *A61K 31/44* (2013.01); *C07D 207/335* (2013.01); *C07D 213/46* (2013.01); *C07D 233/64* (2013.01)

(58) Field of Classification Search
CPC ... C07C 311/21; A61K 31/4164; A61K 31/44; C07D 207/335; C07D 213/46; C07D 233/64
See application file for complete search history.

(56) References Cited

U.S. PATENT DOCUMENTS

2007/0238733 A1  10/2007 Joshi et al.
2010/0184739 A1   7/2010 Sheth et al.
2014/0128352 A1   5/2014 Brand et al.

FOREIGN PATENT DOCUMENTS

| WO | 0027823 | 5/2000 |
| WO | WO2004/035545 | * 4/2004 |
| WO | 2006002421 A2 | 1/2006 |
| WO | 2013192165 A2 | 12/2013 |
| WO | 2015004212 A1 | 1/2015 |

OTHER PUBLICATIONS

International Search Report issued in PCT/US2016/017504, dated Jun. 16, 2016.

* cited by examiner

*Primary Examiner* — Timothy R Rozof
(74) *Attorney, Agent, or Firm* — Heslin Rothenberg Farley & Mesiti, P.C.; Philip Hansen

(57) ABSTRACT

Methods and compositions for treating lysosomal storage disorders are disclosed. The methods involve administering a genus of benzenesulfonamides, particularly N-[3-(aminosulfonyl)phenyl]-benzamides and heteroarylamides. A genus of suitable compounds is shown in formula 1:

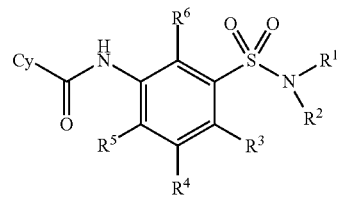

28 Claims, No Drawings

BENZENESULFONAMIDE UPREGULATORS OF NPC1 FOR NEIMANN-PICK DISEASE AND OTHER LYSOSOMAL STORAGE DISORDERS

CROSS-REFERENCE TO RELATED APPLICATIONS

This application is the National Phase filing under 35 U.S.C. § 371 of International Application No. PCT/US2016/017504, filed Feb. 11, 2016, and published as WO 2016/130774 A1 on Aug. 18, 2016, which claims priority from U.S. provisional application 62/114,566, filed Feb. 11, 2015, the entire contents of both of which are incorporated herein by reference in their entirety.

GOVERNMENT RIGHTS STATEMENT

This invention was made with government support under grant numbers MH089537, MH089375, and DK075331 awarded by National Institutes of Health. The government has certain rights in the invention.

BACKGROUND OF THE INVENTION

Technical Field

The present application relates generally to methods and compositions for treating lysosomal storage disorders. The methods involve administering a genus of benzenesulfonamides, particularly N-[3-(aminosulfonyl)phenyl]-benzamides and heteroarylamides.

Background Information

Lysosomal storage disorders, also known as lysosomal storage diseases (LSDs), are a group of approximately 60 relatively uncommon inherited metabolic disorders that result from a deficiency of a particular lysosomal protein. Because most lysosomal hydrolases work sequentially to remove terminal residues from their substrates, a deficiency of one enzyme can cause the components of an entire catabolic pathway to accumulate, since the substrates for hydrolysis by downstream lysosomal enzymes in the pathway are no longer available. The undigested material remains trapped in lysosomes and is visible as deposits in grossly enlarged compartments. Disorders in this group are classified according to their accumulated substrates: mucopolysaccharides, glycoproteins, glycogen, or sphingolipids. Individually, LSDs occur with incidences of less than 1:100,000; however, as a group the incidence is about 1:5,000-1:10,000. Most of these disorders are autosomal recessively inherited such as Niemann-Pick disease, type C (NPC), however a few are X-linked recessively inherited, such as Fabry disease and Hunter syndrome (MPS II).

A recent review [Nature Reviews Neurology 9, 583 (2013)] sets forth the sixty-or-so disorders that are currently considered lysosomal storage diseases. A few of them are described below in some further detail.

Niemann-Pick disease refers to a group of inherited severe metabolic disorders in which cholesterol, sphingomyelin, and other lipids accumulate in lysosomes. The severe form is fatal in toddlerhood; people with milder forms may live into their teens or young adulthood. Niemann-Pick type C is biochemically, genetically and clinically distinct from Niemann-Pick Types A and B. In Types A & B, there is complete or partial deficiency of acid sphingomyelinase; in Niemann-Pick type C, the protein product of the major mutated gene NPC1 is not an enzyme but appears to function as a transporter in the endosomal-lysosomal system, whose deficiency leads to an accumulation of cholesterol, sphingolipids, gangliosides, and fatty acids in the endosomal-lysosomal system. NPC is always fatal. The majority of children with NPC die before age 20 (many die before the age of 10). It is extremely rare for any person with NPC to reach age 40. Progressive neurological disease is the hallmark of Niemann-Pick type C disease, and is responsible for disability and premature death in all cases beyond early childhood. Classically, children with NPC may initially present with delays in reaching normal developmental milestones skills before manifesting cognitive decline. Neurological signs and symptoms include uncoordinated limb movements, slurred speech, difficulty in swallowing, tremor, epilepsy, vertical supranuclear palsy, dystonia, ptosis, microcephaly, psychosis, progressive dementia, progressive hearing loss, bipolar disorder, major and psychotic depression that can include hallucinations, delusions, mutism, or stupor. In the terminal stages of Niemann-Pick type C disease, the patient is bedridden, with complete ophthalmoplegia, severe dementia and loss of volitional movement.

Fabry disease is a lysosomal storage disease that is inherited in an X-linked manner. Fabry disease can cause a wide range of systemic symptoms. Classically affected males, who have little, if any, α-Galactosidase A activity, progressively accumulate the neutral glycosphingolipid, globotriaosylceramide (GL-3), primarily in the lysosomes of vascular endothelial cells of the heart, liver, kidneys, skin, and brain. Onset of the classic disease phenotype occurs during childhood or adolescence and is characterized by severe acroparesthesias, angiokeratoma, corneal and lenticular opacities, and hypohidrosis. With advancing age, vascular disease of the heart, kidneys, and brain leads to early demise during the 4th or 5th decade of life.

Farber disease (also known as Farber's lipogranulomatosis, ceramidase deficiency, "Fibrocytic dysmucopolysaccharidosis," and "Lipogranulomatosis") is a rare autosomal recessive disorder marked by a deficiency in acid ceramidase that causes an accumulation of ceramides leading to abnormalities in the joints, liver, throat, tissues and central nervous system. Disease onset is typically in early infancy but may occur later in life. Children who have the classic form of Farber disease develop symptoms within the first few months of life. These symptoms may include developmental delay and voice, joint, and skin problems. The liver, heart, lungs, and kidneys may also be affected. Patients with breathing difficulty may require a breathing tube. Most children with Farber disease die by age 2, usually from lung disease. In one of the most severe forms of the disease, hepatosplenomegaly can be diagnosed soon after birth. Children born with this form of the disease usually die within 6 months.

Gaucher's disease, the most common of the lysosomal storage diseases, is caused by a hereditary deficiency of the enzyme glucocerebrosidase, which leads to the accumulation of glucosylceramide, most commonly in macrophages in the bone marrow as well as in certain organs. Type I (or non-neuropathic Gaucher) is the most common form of the disease and does not affect the central nervous system. It is most prevalent among persons of Ashkenazi Jewish heritage. The onset of symptoms is variable and may include hepatosplenomegaly, skeletal weakness and bone disease, thrombocytopenia, anemia, and fatigue. Depending on disease onset and severity, type I patients may live well into adulthood. Type II (or acute infantile neuropathic Gaucher's disease) typically begins within 6 months of birth. In addition to the symptoms associated with type I disease, type II patients may also present with extensive and progressive brain damage, eye movement disorders, seizures, limb rigidity, and a poor ability to suck and swallow. Affected children usually die by age two. Type III (chronic neuropathic Gaucher) can begin at any time in childhood or even in adulthood. Although type III disease also affects the nervous system, the neurologic component is more slowly progressive compared to the acute or type II version, and patients can live into their early teen years and adulthood.

Krabbe disease (also known as globoid cell leukodystrophy or galactosylceramide lipidosis) is a rare, often fatal degenerative disorder that affects the myelin sheath of the nervous system. It is a form of sphingolipidosis caused by mutations in the GALC gene resulting in deficiency of galactosylceramidase. The condition is inherited in an autosomal recessive pattern. Infants with Krabbe disease are normal at birth. Symptoms begin between the ages of 3 and 6 months, and the disease is generally fatal before age two. Patients with late-onset Krabbe disease tend to have a slower progression of the disease. In the US population, Krabbe disease occurs in about one in 100,000 births; however, a higher incidence, about six in 1,000, has been reported in certain communities in Israel, and Scandinavian countries have comparatively high rates of the disease, reported to be one in 50,000 births.

The LSDs have long served as models for the development of treatment modalities for inherited metabolic diseases. The observation that even very low normal enzyme levels could correct the metabolic defect in cultured fibroblasts from patients affected with various LSDs has led to the successful development of enzyme replacement therapy for Type 1 Gaucher disease and Fabry disease, among others. However, at present there are no treatment options for patients with NPC1 or other storage disorders that present with neuropathology due to the severe problems associated with accessing the central nervous system with proteins or genes.

SUMMARY OF THE INVENTION

The invention is directed to pharmaceutical compositions and methods for upregulating the NPC1 promoter and thereby treating lysosomal storage disorders.

The present invention provides, in a first aspect, a method of treating a lysosomal storage disorder comprising administering a compound of formula I

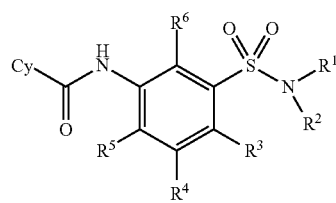

wherein
$R^1$ is selected from hydrogen and $(C_1-C_6)$alkyl;
$R^2$ is selected from $(C_1-C_6)$alkyl, optionally substituted benzyl, meta-substituted phenyl and para-substituted phenyl, wherein substituents on the benzyl or phenyl are selected from $(C_1-C_6)$alkyl, halogen, halo$(C_1-C_6)$alkyl, $(C_1-C_6)$alkoxy, and cyano; or
$R^1$ and $R^2$, together with the nitrogen to which they are attached, form an optionally substituted and/or fused heterocycle;
$R^3$, $R^4$, $R^5$ and $R^6$ are independently selected from hydrogen, $(C_1-C_6)$alkyl, halogen, hydroxy, cyano, nitro, amino, halo$(C_1-C_6)$alkyl, $(C_1-C_6)$alkoxy, and $(C_1-C_6)$alkoxy substituted with an amine or saturated nitrogen heterocycle;
Cy is chosen from adamantyl, optionally substituted monocyclic aryl, and optionally substituted monocyclic heteroaryl, with the proviso that when $R^2$ is $(C_1-C_6)$alkyl, Cy is not unsubstituted aryl or heteroaryl.

The present invention provides, in a second aspect, pharmaceutical formulations of the compounds of formula I as described below.

The present invention provides, in a third aspect, specific compounds within genus I as described below.

DETAILED DESCRIPTION OF THE INVENTION

It has been found that compounds of formula I

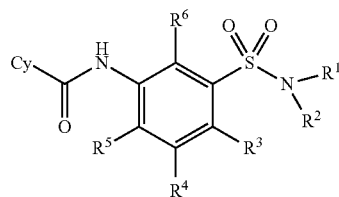

are useful for treating lysosomal storage disorders.

In some embodiments of the formula I, Cy is optionally substituted pyrazole, pyrrole, thiazole, imidazole, oxazole, pyridine, pyridazine, pyrimidine, thiophene, furan, or phenyl. In some embodiments, Cy is an optionally substituted pyrrole, an ortho-substituted phenyl, a meta-substituted phenyl, or an optionally substituted pyridine, wherein the substituents on the pyrrole, phenyl or pyridine ring are selected from $(C_1-C_6)$alkyl, $(C_1-C_6)$acyl, halo$(C_1-C_6)$alkyl, $(C_1-C_{10})$oxaalkyl and halogen. It is to be understood that the recitation of ortho-substituted, meta-substituted and (in other contexts) para-substituted means that a substituent will be found at the denominated position. Unless further explicitly restricted, (e.g. "monosubstituted at the ortho position"), it is not meant to imply that no other substituents will be found anywhere else on the ring.

In some embodiments of the formula I, $R^1$ and $R^2$ taken together do not form a ring. In these embodiments, $R^1$ may be selected from hydrogen and $(C_1-C_6)$alkyl. In some embodiments, $R^2$ may be meta- or para-substituted phenyl, and the meta and para substituents may be chosen from bromo, cyano and acetyl. In some embodiments, $R^1$ is $(C_1-C_6)$alkyl and $R^2$ is $(C_1-C_6)$alkyl.

In some embodiments of the formula I, $R^1$ and $R^2$, together with the nitrogen to which they are attached, form an optionally substituted and/or fused heterocyclic ring. In these embodiments, the ring may be a saturated nitrogen heterocycle, for example, a pyrrolidine, piperidine, azepine, morpholine or piperazine, or it may be a fused heterocycle such as tetrahydrobenzoazepine, tetrahydroquinoline, tetrahydroisoquinoline, indoline or isoindoline.

In some embodiments of the formula I, $R^3$ is selected from hydrogen, $(C_1\text{-}C_6)$alkyl, halogen, hydroxy, cyano, nitro, amino, halo$(C_1\text{-}C_6)$alkyl, $(C_1\text{-}C_6)$alkoxy, and $(C_1\text{-}C_6)$alkoxy substituted with an amine or saturated nitrogen heterocycle; and $R^4$, $R^5$ and $R^6$ are independently selected from hydrogen and fluorine. Examples of a $(C_1\text{-}C_6)$alkoxy substituted with an amine or saturated nitrogen heterocycle would be dimethylaminopropoxy and 2-(pyrrolidin-1-yl)ethoxy. Usually $(C_1\text{-}C_{10})$oxaalkyl and the alkyl portion of $(C_1\text{-}C_6)$alkoxy substituted with an amine or saturated nitrogen heterocycle will be linear. In some embodiments, $R^3$ is selected from hydrogen, methyl, ethyl, methoxy and hydroxy; $R^4$ and $R^6$ are hydrogen; and $R^5$ is hydrogen or fluorine.

As used herein, the term "optionally substituted" may be used interchangeably with "unsubstituted or substituted". The term "substituted" refers to the replacement of one or more hydrogen atoms in a specified group with a specified radical. For example, substituted aryl, heterocyclyl etc. refer to aryl or heterocyclyl wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], carboxamido [—C(=O)NH$_2$], alkyl aminocarbonyl [—C(=O)NH-alkyl], cyano, acetoxy, nitro, amino, alkylamino, dialkylamino, dialkylaminoalkyl, dialkylaminoalkoxy, heterocyclylalkoxy, mercapto, alkylthio, sulfoxide, sulfone, sulfonylamino, alkylsulfinyl, alkylsulfonyl, benzyl, heterocyclyl, phenoxy, benzyloxy, heteroaryloxy, aminosulfonyl, amidino, guanidino, and ureido.

Many of the compounds described herein are known in the literature and may be purchased from commercial sources. Compounds not commercially available may be synthesized by the following route:

Scheme 1

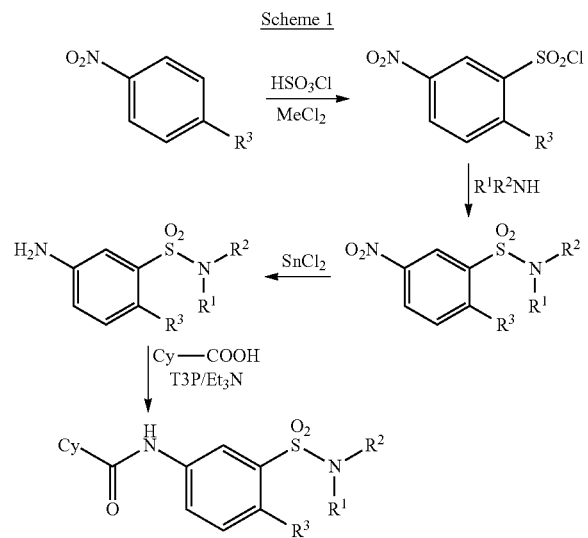

The person of skill will recognize that the reagents shown above are exemplary and can be replaced by analogous reagents well known in the art for accomplishing the same transformation. For example, CyCOOH can be condensed with the aniline by any of the common reagents used in amide and peptide synthesis. Similarly, the nitro group can be reduced with hydrogen and catalyst or another metal/acid combination. An exemplary synthesis is as follows.

Preparation of N-(3-(N-(4-bromophenyl)sulfamoyl)-4-methoxyphenyl)-4-methylnicotinamide Step 1.

A solution of 1-methoxy-4-nitrobenzene A (6.2 g, 41 mmol) in ClCH$_2$CH$_2$Cl (5 mL) was cooled to 0° C. and treated with dropwise addition of chlorosulfonic acid (4 mL, 6 mmol). The reaction was warmed to RT, refluxed for 2 hr, and then cooled. Water was added carefully to quench excess chlorosulfonic acid. Precipitation of solids was observed that dissolved back on addition and stirring of the mixture with chloroform. The organic layer was separated, dried (MgSO$_4$), filtered, and concentrated to provide 2-methoxy-5-nitrobenzene-1-sulfonyl chloride B (1.78 g, 7.07 mmol, 17.5% yield).

Step 2.

B (1.7 g, 6.8 mmol) was treated with 4-bromoaniline (1.7 g, 10 mmol) in pyridine (10 mL). The reaction was attached to a reflux condenser and stirred for 16 hr at 90° C. Most of the pyridine was removed via rotary evaporation; the residue was diluted with EtOAc and then washed with water, and then brine. The organic layer was separated, dried with (MgSO$_4$), filtered, concentrated, and purified to yield 1.7 g (65%) of C. LC/MS (Agilent system) Retention time $t_1$ (short)=3.50 min, MS (ESI) m/z calculated for $C_{26}H_{22}Br_2N_4NaO_{10}S_2$ [2M+Na]$^+$796.9, found 796.8. $^1$H NMR (400 MHz, DMSO-d$_6$) δ ppm 10.54 (br. s., 1H), 8.49 (d, J=2.7 Hz, 1H), 8.45 (dd, J=8.4 Hz, J=2.8 Hz, 1H), 7.38-7.43 (m, 3H), 7.09-7.02 (m, 2H), 4.01 (s, 3H).

Step 3.

C (0.90 g, 2.30 mmol) was dissolved in EtOH (24 mL), treated with tin (II) chloride dihydrate (2.1 g, 9.3 mmol). The reaction was refluxed for 1 hr, cooled, and treated with 1 N NaOH till pH~6. A white suspension, presumably consisting of tin salts, was observed. EtOAc was added and the mixture stirred overnight vigorously. The aqueous layer was still a white suspension. The mixture was filtered through celite, the organic layer was separated, dried (MgSO$_4$), filtered, and concentrated. Purification by flash silica gel chromatography with an isocratic 35% EtOAc/hexanes solvent system separated a closely eluting non polar compound to provide pure aniline D (0.56 g, 1.57 mmol, 67% yield). LC/MS (Agilent system) Retention time $t_1$ (short)=2.78 min, MS (ES1) m/z calculated for $C_{13}H_{14}BrN_2O_3S$ [M+H]$^+$ 357.0, found 356.9. $^1$H NMR (400 MHz, DMSO-d6) δ 9.96 (s, 4H), 7.44-7.33 (m, 8H), 7.09-6.97 (m, 12H), 6.87 (d, J=8.8 Hz, 4H), 6.72 (dd, J=8.7, 2.8 Hz, 4H), 5.02 (s, 10H), 4.03 (q, J=7.1 Hz, 1H), 3.71 (s, 12H), 1.99 (s, 1H), 1.17 (t, J=7.1 Hz, 1H). $^1$H NMR (400 MHz, DMSO-d6) δ 9.96 (s, 1H), 7.42-7.33 (m, 2H), 7.07-6.98 (m, 3H), 6.87 (d, J=8.8 Hz, 1H), 6.72 (dd, J=8.7, 2.8 Hz, 1H), 5.02 (s, 2H), 3.71 (s, 311).

Step 4.

5-Amino-N-(4-bromophenyl)-2-methoxybenzenesulfonamide D (70 mg, 0.20 mmol) was dissolved in DMF and treated with 4-methylnicotinic acid (81 mg, 0.59 mmol), 2,4,6-tripropyl-1,3,5,2,4,6-trioxatriphosphinane 2,4,6-trioxide (0.37 g, 0.59 mmol) (T3P®), and triethylamine (0.11 mL, 0.78 mmol). The reaction stirred at 60° C. for 48 hr. After cooling the mixture, which had turned into a gel, was diluted with water and extracted with EtOAc. The organic layer was separated, concentrated, and purified by C18 reverse phase column chromatography to yield N-(3-(N-(4-bromophenylsulfamoyl)-4-methoxyphenyl)-4-methylnicotinamide: 32 mg (0.07 mmol, 34%): LC/MS (Agilent system) Retention time $t_1$ (long)=4.13 min, MS (ESI) m/z calculated for $C_{20}H_{19}BrN_3O_4S$ [M+H1]$^+$ 476.0 found 476.0; $^1$H NMR (400 MHz, DMSO-d$_6$) δ 10.58 (s, 1H), 10.17 (s, 1H), 8.72

(s, 1H), 8.58 (d, J=5.1 Hz, 1H), 8.25 (d, J=2.6 Hz, 1H), 7.88 (dd, J=9.0, 2.7 Hz, 1H), 7.45 (d, J=5.2 Hz, 1H), 7.43-7.37 (m, 2H), 7.19 (d, J=9.0 Hz, 1H), 7.10-7.03 (m, 2H), 3.86 (s, 3H), 2.44 (s, 311); HRMS (ESI) m/z calculated for $C_{20}H_{19}BrN_3O_4S$ [M+H]+476.0274 found 476.0284.

As used herein, "treatment" or "treating," or "palliating" or "ameliorating" are used interchangeably. These terms refer to an approach for obtaining beneficial or desired results including but not limited to therapeutic benefit. By therapeutic benefit is meant amelioration of the underlying disorder. Also, a therapeutic benefit is achieved with the amelioration of one or more of the physiological symptoms associated with the underlying disorder such that an improvement is observed in the patient, notwithstanding that the patient may still be afflicted with the underlying disorder. For example, "treating NPC" means alleviating at least one symptom associated with NPC; it is not required that the patient no longer exhibit any symptoms of NPC or that lysosome function be brought to a normal state. The compositions may be administered to a patient at risk of developing a particular disease, or to a patient reporting one or more of the physiological systems of a disease, even though a diagnosis of this disease may not have been made.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of". The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition or method. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method that "comprises", "has", "includes" or "contains" one or more steps or elements possesses those one or more steps or elements, but is not limited to possessing only those one or more steps or elements.

The formulations related to this invention include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Preferred unit dosage formulations are oral unit dosage forms containing an effective dose, or an appropriate fraction thereof, of the active ingredient.

Formulations for parenteral administration include aqueous and non-aqueous sterile injection solutions, which may contain anti-oxidants, buffers, bacteriostats and solutes that render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

It should be understood that in addition to the ingredients particularly mentioned above, the formulations related to this invention may include other agents conventional in the art. For example those suitable for oral administration may include other therapeutic ingredients, anti-caking agents, preservatives, sweetening agents, colorants, flavors, desiccants, plasticizers, dyes, disintegrants, lubricants and the like.

Lysosomal storage disorders include: (1) sphingolipidoses such as Fabry disease; Farber lipogranulomatosis; Gaucher disease types I, II and III; Niemann-Pick disease types A and B; GM1 gangliosidosis; GM2-gangliosidosis (Sandhoff); GM2-gangliosidosis (Tay-Sachs); GM2-gangliosidosis (GM2-activator deficiency); GM3-gangliosidosis; metachromatic leukodystrophy; and sphingolipid-activator deficiency; (2) mucopolysaccharidoses such as MPS I (Schele, Hurler-Schele and Hurler disease); MPS II (Hunter); MPS IIIA (Sanfilippo A); MPS IIIB (Sanfilippo B); MPS IIIC (Sanfilippo C); MPS IIID (Sanfilippo D); MPS IVA (Morquio syndrome A); MPS IVB (Morquio syndrome B); MPS VI (Maroteaux-Lamy); MPS VII (Sly disease); and MPS IX; (3) oligosaccharidoses such as α-mannosidosis; β-mannosidosis; fucosidosis; aspartylglucosaminuria; Schindler disease; sialidosis; galactosialidosis; mucolipidosis II (I-cell disease); and mucolipidosis III; (4) glycogen storage diseases such as Pompe disease; and (5) integral membrane protein disorders such as cystinosis; Danon disease; action myoclonus-renal failure syndrome; Sailia disease; Niemann-Pick disease type C1; and Mucolipidosis IV. Also often included in the class of lysosomal storage disorders are Haitia-Santavuori; Jansky-Bielschowsky; Spielmeyer-Sjogren; Parry; Hermansky-Pudlak diseases types 1-8; Griscelli 1, 2 and 3; and Chediak-Higashi disease.

Lysosomal storage disorders of particular interest are Niemann-Pick C, Fabry Disease, Farber Disease, Gaucher's Disease, Sanfilippo's and other mucopolysaccharidoses.

Turning to Niemann-Pick C, 95% of patients have mutations within the NPC1 gene, which codes for a large transmembrane glycoprotein present within the membranes of late endosomal vesicles that are mostly Rab9-GTPase positive. The NPC1 protein has been established as a homologous eukaryotic member of the resistance-nodulation-division (RND) family of prokaryotic permeases with a "multidrug" transmembrane efflux pump function. With thirteen transmembrane domains, three large heavily glycosylated endosomal loops, several smaller cytoplasmic loops, and a C-terminal cytoplasmic tail, the protein also has a domain with strong topological resemblance to the sterol-sensing domains (SSD) of 3-hydroxy-3-methylglutaryl-coenzyme A reductase (HMG-R) and sterol regulatory element binding protein cleavage-activating protein (SCAP), which both play a critical role in cholesterol homeostasis. This structural homology is in line with the biochemical hallmark and diagnostic marker of NPC disease: impaired cholesterol egress out of late endosomes, which can be assessed by using the fluorescent probe filipin to bind free unesterified cholesterol. A possible mechanistic proposal (to which the inventors do not wish to be held) is that esterified or free cholesterol, associated with LDL or from the plasma membrane, enters the cell via receptor mediated endocytosis. It is subsequently delivered into the late endosomal/lysosomal organelles where lysosomal acid lipase hydrolyses the esterified cholesterol to liberate free cholesterol. Extrusion of free cholesterol into the cytosol is carried out by a two-step mechanism, first through binding with the lysosomal protein HE1, a soluble protein encoded by the NPC2 gene that accounts for the remaining 5% of mutations of NPC disease, which subsequently transfers its cholesterol cargo to NPC1 protein in the late endosomal membrane.

Out of the ~200 mutations causing NPC disease, a majority of them are missense mutations that are distributed throughout the length of the NPC1 protein. One of the most prevalent mutations is the I1061T allele, which, although it codes for a functional protein, has a propensity for misfolding that leads to its being targeted for endoplasmic reticulum-associated degradation.

We have now found a genus of small molecules that are able to upregulate overall cellular levels of endogenous mutant NPC1 and/or the late endosomal transport protein Rab9 and in turn ameliorate the NPC disease phenotype. A reasonable explanation for the observed results is that upregulation of endogenous mutant NPC1 proteins increases the fraction of properly folded NPC1 protein that can escape the endoplasmic reticulum and be targeted to the late endosomal/lysosomal system. This, in turn, reduces the percentage of total mutant protein tagged for degradation. Increased trafficking of the NPC1 protein to the late endosome improves the blocked egress of lipids out of that compartment and normalizes the disease phenotype. The small GTPase Rab9 is a modulator of retrograde transport from the late endosome to the TGN, which is the defective pathway in NPC1 disease. Overexpression of Rab9 in NPC1 disease fibroblasts bypasses the requirement for NPC1 protein function and restores transport from the late endosome to the TGN, in effect "suppressing" the NPC1 lipid transport block phenotype.

Using Huh7 human hepatoma cell lines that stably express either a Rab9-promoter or NPC1-reporter construct, we have found that compounds of formula I demonstrate excellent activity in clearing cholesterol and the glycosphingolipid globotriaosylceramide (GL-3) from NPC1 patient fibroblast cell lines. Upregulating NPC1 or Rab9 provides an approach to treating Niemann-Pick type C disease, as well as other lysosomal storage diseases as discussed below.

The reagents and solvents used were commercial anhydrous grade and used without further purification. The column chromatography was carried out over silica gel (100-200 mesh). $^1$H NMR spectra were recorded with a Varian 400 MHz spectrometer from solutions in $CDCl_3$ and DMSO-$d_6$. Chemical shifts in $^1$H NMR spectra are reported in parts per million (ppm, δ) with solvent peaks as internal. Molecular weight confirmation was performed using an Agilent 6224 Time-Of-Flight Mass Spectrometer (TOF, Agilent Technologies, Santa Clara, Calif.). A 3 minute gradient from 5 to 100% Acetonitrile in water (0.03% formic acid) was used with a 5.1 minute run time at a flow rate of 0.4 mL/min. A Waters Atlantis T3 C18 column (1.8 micron, 2.1×50 mm) was used at a temperature of 25° C. Confirmation of molecular formula was confirmed using electrospray ionization in the positive mode with the Agilent Masshunter software (version B.02).

Assays qHTS of Rab9 Promoter-Luciferase Reporter Gene Assay. For the primary screen, a promoter assay was developed by engineering a vector using approximately 1.5 kb of the Rab9 promoter to drive the expression of the firefly luciferase reporter gene. Thus, Rab9 promoter activation results in luciferase expression. This vector was used to generate Huh7 cell lines stably expressing the Rab9-luciferase vector. These cells were propagated and maintained in medium containing RPMI-1640 supplemented with 10% FBS, 2 mM L-glutamine, and 50 ug/mL penicillin/streptomycin. Cells were plated for assays in OPTI-MEM I reduced-serum medium supplemented with 10% FBS at 1,500 cells/well in 5 μL in 1,536-well white opaque plates with 23 nL/well of test compound in DMSO solution. The assay plates were incubated at 37° C. for 24 hours, after which 3 μL/well BriteLite plus luciferase detection reagent mixture (Perkin Elmer) was added. Luminescence signal was measured in a ViewLux plate reader (Perkin Elmer) after a 10 minute incubation at room temperature.

qHTS of NPC1 Promoter-Luciferase Reporter Gene Assay. For the second primary screen, a promoter assay was developed by engineering a vector using approximately 1.5 kb of the NPC1 promoter to drive the expression of the firefly luciferase reporter gene. Thus, NPC1 promoter activation results in luciferase expression. This vector was used to generate Huh7 cell lines stably expressing the NPC1-luciferase vector. These cells were maintained in medium containing RPMI-1640 supplemented with 10% FBS, 2 mM L-glutamine, and 50 μg/mL penicillin/streptomycin. Cells were plated for assays in OPTI-MEM I reduced-serum medium supplemented with 10% FBS at 1,500 cells/well in 5 μL in 1,536-well white opaque plates with 23 nL/well of test compound in DMSO solution. The assay plates were incubated at 37° C. for 24 hours, after which 3 μL/well BriteLite plus luciferase detection reagent mixture (Perkin Elmer) was added. Luminescence signal was measured in a ViewLux plate reader (Perkin Elmer) after a 10 minute incubation at room temperature.

Confirmation Assay of Rab9 Promoter Activators: Renilla Luciferase. The confirmation assay was carried out using an assay in which the Rab9 promoter drives the expression of a different luciferase protein from the one used in the primary screen. The Rab9 promoter was cloned in front of the renilla luciferase reporter gene, therefore Rab9 promoter activation results in renilla luciferase expression. This vector was used to generate Huh7 cell lines stably expressing the Rab9-renilla luciferase vector. These cells were propagated and maintained in medium containing RPMI-1640 supplemented with 10% FBS, 2 mM L-glutamine, and 50 μg/mL penicillin/streptomycin. Cells were plated for assays in OPTI-MEM I reduced-serum medium supplemented with 10% FBS at 1,500 cells/well in 5 μL in 1,536-well white opaque plates and then 23 nL/well of compound in DMSO solution were added through pin transfer. The assay plates were incubated at 37° C. for 24 hours. The Amplite luciferase reporter gene assay kit was purchased from ABD Bioquest and prepared/stored according to manufacturer's recommendations. Luminescence signal was measured in a ViewLux plate reader (Perkin Elmer) after a 10 minute incubation at room temperature.

Confirmation Assay of NPC1 Promoter Activators: Renilla Luciferase. The confirmation assay was carried out using an assay in which the NPC1 promoter drives the expression of a different luciferase protein from the one used in the primary screen. The NPC1 promoter was cloned in front of the renilla luciferase reporter gene. NPC1 promoter activation results in renilla luciferase expression. This vector was used to generate Huh7 cell lines stably expressing the NPC1-renilla luciferase vector. These cells were propagated and maintained in medium containing RPMI-1640 supplemented with 10% FBS, 2 mM L-glutamine, and 50 μg/mL penicillin/streptomycin. Cells were plated for assays in OPTI-MEM I reduced-serum medium supplemented with 10% FBS at 1,500 cells/well in 5 μL in 1,536-well white opaque plates and then 23 nL/well of compound in DMSO solution were added through pin transfer. The assay plates were incubated at 37° C. for 24 hours. The Amplite luciferase reporter gene assay kit was purchased from ABD Bioquest and prepared/stored according to manufacturer's recommendations. Luminescence signal was measured in a ViewLux plate reader (Perkin Elmer) after a 10 minute incubation at room temperature.

Cytotoxicity Assay. A cytotoxicity assay was run in order to distinguish compounds that demonstrated toxicity against the NPC1-firefly luciferase cells. Cells were propagated and maintained in medium containing RPMI-1640 supplemented with 10% FBS, 2 mM L-glutamine, and 50 μg/mL penicillin/streptomycin. Cells were plated for assays in OPTI-MEM I reduced-serum medium supplemented with 10% FBS. Cells were seeded at 4,000 cells/well by adding 3 μL into 1,536-well white opaque plates, and then 23 nL/well of test compound in DMSO solution were added through pin transfer. The assay plates were incubated at 37° C. for 48 hours, after which 3 μL/well of CellTiter Glo (Perkin Elmer) was added. Luminescence signal was measured in a ViewLux plate reader (Perkin Elmer) after a 5 minute incubation at room temperature.

Biochemical Renilla Luciferase Counter assay. An orthogonal assay was run to exclude any compounds that promoted renilla luciferase signal by stabilizing the renilla protein. Briefly, 3 μL of 0.01 mM D-Luciferin and 0.01 mM ATP was dispensed into a 1536 well white, solid bottom plate. Through pinning, 23 nL of compound was added; PTC124 (3-[5-(2-Fluorophenyl)-1,2,4-oxadiazol-3-yl]benzoic acid) served as the control. After a 10 min incubation at room temperature, 1 μL of Luciferase was added, after which the plate was immediately read on the ViewLux for a luminescent read-out. The final concentrations of all components was as follows: 0.01 mM D-Luciferin, 0.01 mM ATP, 10 nM *P. pyralis* Luciferase, 1 M Mg-acetate, 0.01% Tween-20 and 0.05% BSA.

VTB-GL-3 assay. Accumulation of the neutral glycosphingolipid globotriaosylceramide (GL-3) in lysosomes is the hallmark of Fabry disease but has also been observed in other lysosomal storage disorders, including NPC disease. Clearance of GL-3 from organs such as the kidney and liver corresponds to an improvement in Fabry disease prognosis. The lipid can be detected using the B subunit of *Escherichia coli* verotoxin (VTB), which has high specificity and avidity for both the oligosaccharide and ceramide moieties of GL-3. Purified recombinant VTB was produced from bacteria and coupled to the fluorochrome Alexa594 for cell detection studies. After 48-72 hour treatment with test compound, cells were washed with phosphate buffered saline (PBS), fixed with phosphate-buffered formalin for 30 min at 4° C., washed with saline 2×5 min, and incubated with 1 mg/mL Alexa594-VTB in PBS for 45 min. Cells were then washed with saline 2×5 min, mounted with fluoromount, and scored under the 40× magnification filter using the integrated morphometry function in the Metavue program (Molecular Devices).

As an example, VTB can be used to assess the level of lipid storage correction in NPC cells following treatment with various compounds described here. Wild type (Wt) and NPC3 cells were treated with two compounds for 3 days and then processed for VTB staining as described above. Untreated NPC3 cells show intense staining whereas Wt cells show minimal storage of material as expected. Upon treatment with compounds of example 1 and example 36, the storage of lipid material in NPC3 cells is greatly reduced with no effect on Wt cells. Quantitation of the fluorescence intensity of the VTB staining indicates that the two compounds can reduce lipid storage in NPC3 cells by greater than 90%.

Compounds of formula I were tested in the screens described above with the following results:

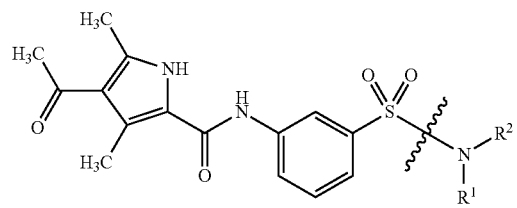

TABLE 1

| # | NR¹R² | NPC1 EC50 μM | NPC1 Eff. % | Rab9 EC50 μM | Rab9 Eff. % |
|---|---|---|---|---|---|
| 1 | —N(CH₃)₂ | 6.6-7.7 | 68-83 | 6.1 | 148 |
| 2 | —NEt₂ | 7.7 | 155 | 8.7 | 181 |
| 3 | pyrrolidinyl | 6.1 | 112 | 7.7 | 149 |
| 4 | piperidinyl | 2.7 | 163 | 1.7 | 134 |
| 5 | azepanyl | 2.7-2.9 | 196-205 | 2.0 | 153 |
| 6 | N-methylpiperazinyl | Inactive | | 10.9 | 82 |
| 7 | morpholinyl | 8.3 | 84 | 12.2 | 122 |

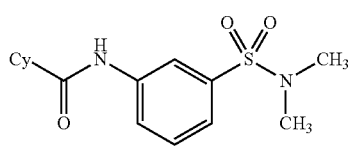
TABLE 2
| # | Cy | NPC1 EC50 μM | NPC1 Eff. % | Rab9 EC50 μM | Rab9 Eff. % |
|---|---|---|---|---|---|
| 8 | 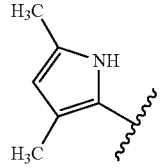 [SMILES: *c1[nH]c(C)cc1C] | 17.2[b] | 48 | 38.7[a] | 82 |
| 9 | 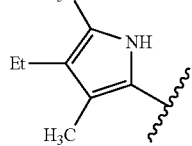 | 8.6[a] | 47 | Inactive | |
| 10 | 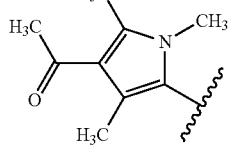 | 21.6[a] | 83 | Inactive | |
| 13 | p-tolyl | Inactive | | 6.9 | 54 |
| 14 | o-tolyl | 4.8 | 51 | 17.3 | 114 |
| 15 | m-tolyl | 6.1 | 81 | 19.4[b] | 75 |
| 16 | 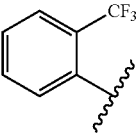 | 1.2 | 125 | 1.4 | 155 |
| 17 | 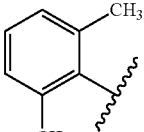 | 5.4 | 127 | 5.5 | 131 |
| 18 | 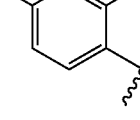 | 5.4 | 79 | 12.2 | 97 |
| 19 | 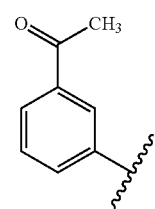 [SMILES: *c1cccc(C(C)=O)c1] | 8.6[b] | 40 | 19.4[b] | 94 |
TABLE 2-continued
| # | Cy | NPC1 EC50 μM | NPC1 Eff. % | Rab9 EC50 μM | Rab9 Eff. % |
|---|---|---|---|---|---|
| 20 | 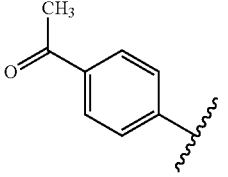 [SMILES: *c1ccc(C(C)=O)cc1] | Inactive | | 10.9 | 110 |
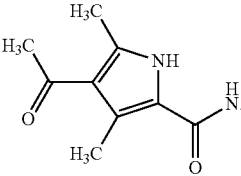
TABLE 3
| # | R³ | R² | NPC1 EC50 μM | Eff. % |
|---|---|---|---|---|
| 23 | H | p-Br, m-F Ph | 15.4 | 71[a] |
| 31 | H | m-CN Ph | Inactive | |
| 32 | H | p-Br Ph | 4.3 | 80 |
| 33 | Et | m-CN Ph | 2.7 | 140 |
| 34 | Me | p-Br Ph | 1.7 | 248 |
| 35 | Et | p-Br Ph | 0.7 | 208 |
| 36 | OMe | p-Br Ph | 0.7 | 150 |
| 38 | Et | p-CN Ph | 3.4 | 259 |
| 40 | OMe | m-CN Ph | 0.9 | 129 |
| 41 | OMe | p-CN Ph | 8.7 | 100 |
| 54 | O(CH₂)₃N(CH₃)₂ | p-Br Ph | | |
| 58 | OMe | p-Cl Ph | | |
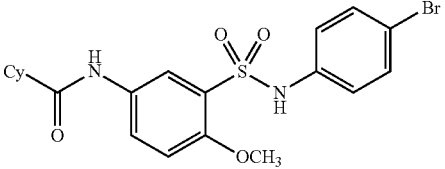

TABLE 4

| # | Cy | NPC1-renilla EC$_{50}$ μM | Eff. % | Renilla Enzyme IC$_{50}$ μM |
|---|---|---|---|---|
| 42 | 2,3-dimethyl-pyrrole (H$_3$C, NH, H$_3$C) | 2.7 | 119 | Inactive |
| 43 | pyrrole (NH) | 4.3 | 88 | Inactive |
| 44 | 3-acetyl-2,4,5-trimethyl-1-methyl-pyrrole | 0.5 | 245 | 19.40 |
| 45 | phenyl | 1.1 | 223 | Inactive |
| 46 | 2,6-dimethylphenyl | 1.1 | 192 | 54.68[a] |
| 47 | Adamantyl | 2.7 | 80 | Inactive |
| 49 | 2-methylpyridin-3-yl | 5.5 | 395 | Inactive |
| 50 | 4-methylpyridin-3-yl | 1.1 | 195 | Inactive |
| 51 | pyridin-3-yl | 2.7 | 257 | 54.68[a] |
| 55 | imidazol-2-yl | | | |
| 56 | imidazol-4-yl | | | |
| 57 | 2-phenyl-imidazol-4-yl (Ph, N, HN) | | | |

[a] These compounds had partial efficacy and/or poor fit at higher concentrations.

Filipin Staining Assay to Detect Free Cholesterol Accumulation in NPC Cells. Compounds were evaluated for their effect on the NPC1 cellular phenotype by staining treated NPC1 patient cell fibroblasts with filipin, which recognizes free unesterified cholesterol. Compounds that upregulate the NPC1 promoter were expected to reduce the filipin staining in treated NPC1 fibroblasts compared to untreated NPC1 fibroblasts, indicating clearance of unesterified cholesterol. Conversely, inhibitors of the NPC1 promoter were expected to increase filipin staining in wild-type fibroblasts, thus indicating the emergence of an NPC-like phenotype. Briefly, cells were grown in lipoprotein-deficient medium for 3-4 days, and then the medium was replaced and supplemented with test compound plus 50 μg/mL low-density lipoprotein (LDL). After 24-48 hours, cells were stained with filipin and scored under the 40× magnification filter using the integrated morphometry function in the Metavue program (Molecular Devices). Test compounds that decreased the intensity of filipin fluorescence to less than 50% of untreated cells are considered of particular interest.

TABLE 5

| Example # | % storage at 1 μM | % storage at 0.1 μM |
|---|---|---|
| 41 | 58 | |
| 38 | 62 | |
| 31 | 56 | |
| 33 | 35 | 43 |
| 45 | 60 | |
| 42 | 47 | 49 |
| 46 | 46 | 26 |
| 53 | 24 | 55 |
| 47 | 33 | |
| 51 | 29 | |
| 40 | 29 | |
| 49 | 30 | |
| 1 | 22 | 40 |
| 36 | 25 | 50 |
| 50 | 25 | 37 |
| 54 | 60 | |
| 55 | 30 | |
| 56 | 48 | 50 |
| 57 | 41 | 70 |
| 58 | 58 | |
| 59 | 40 | |

Additional compounds, not found in previous tables but shown in Table 5, are:

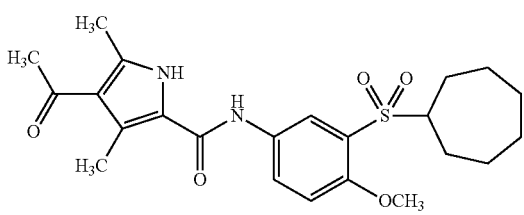 [SMILES: COc1ccc(NC(=O)c2[nH]c(C)c(C(C)=O)c2C)cc1S(=O)(=O)C1CCCCCC1]

Example 53

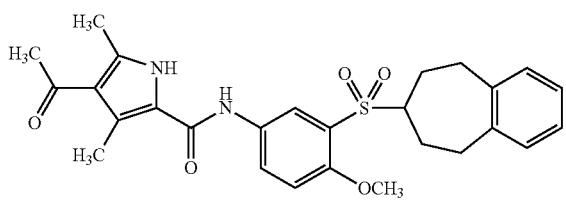 [SMILES: COc1ccc(NC(=O)c2[nH]c(C)c(C(C)=O)c2C)cc1S(=O)(=O)C1CCc2ccccc2CC1]

Example 59

Lactosyl Ceramide staining to monitor sphingolipid transport in NPC cells. The effect of each compound on the sphingolipid transport defect seen in NPC1 fibroblasts was assessed in cells treated with compound for 48-72 hours using the fluorescent probe BODIPY-lactosylceramide (LacCer). This glycolipid localizes entirely to the Golgi apparatus in Wt cells after 1 hour but exhibits only endosomal staining in NPC1 cells. This mislocalization can be corrected and Golgi localization restored by expression of Wt NPC1 protein or Rab9, thus providing a dynamic view of the endocytic transport pathway. Cells were incubated with 5 µM BODIPY-LacCer/BSA for 45 min at 37° C. in culture medium containing 1% FBS, washed, and further incubated for 1 h at 37° C. in medium containing 1% FBS. Fluorescent lipid present at the plasma membrane was removed by back-exchange with 5% fatty acid-free BSA. Cells were fixed with 3% paraformaldehyde for 20 min at RT and then visualized on a Nikon Eclipse microscope fitted with a charge-coupled-device camera. Images were acquired with MetaVue software and then deconvoluted using AutoDeblur software.

Unlike the VTB assay above that detects the static levels of lipid storage, the Bodipy LacCer probe allows for detection of the recovery/correction of lipid transport from the plasma membrane to the Golgi apparatus as described above. This dynamic assay can be used to determine the level of correction various compounds have on the NPC transport block. NPC3 cells treated with the compounds of examples 1 and 36 show a correction of their block indicated by the accumulation of the probe to the Golgi compared to untreated NPC3 cells. The compound of example 1 at 1 µM reduces percent Golgi location by a statistically significant amount. The compound of example 36 at 10 or 100 nM reduces percent Golgi location by a statistically significant amount.

Efficacy of compounds in treating Fabry Disease was determined by measuring the decrease of GL3 accumulation in the liver and spleen of Fabry mice as described by Ioannou et al. [*Am. J. Hum. Genet.* 68, 14-25 (2001)]. Twenty NPC1 mice, age and sex matched, were separated into 2 groups of 10 mice each. Each mouse received a total of 200 µL of DMA/solutol/saline solution. The compound of example 50 was dissolved in DMA/solutol/saline and given at 30 mg/Kg=750 µg/mouse. Each mouse received three i.p. injections a week for three weeks. At the end of three weeks, the mice were sacrificed and organs collected. The Fabry glycolipid GL-3 was extracted from each tissue and quantitated using a GL-3 ELISA assay [Zeidner et al. *Analytical Biochemistry* 267, 104-113 (1999)]. The liver, heart and kidney of treated mice showed greater than 50% decrease in GL-3 levels. Plasma levels were also lowered, but not as much (30%).

In order to quantify the lysosomal storage in different lysosomal storage diseases we developed a number of toxins that bind to specific types of lipids. The use of recombinant *E. coli* verotoxin subunit B (VTB) for the detection and quantitation of its receptor, globotriaosyl ceramide (GL3) is described above. We re-engineered VTB to include a step-tag II sequence at the C-terminus so that it can be used with a variety of streptavidin-labeled probes. We engineered four different versions of osterolysin A (OlyA) fused to different reporters; GFP, RFP, luciferase, StrepTag. In addition, we constructed a probe based on tetanus toxin fragment C (TTC) that binds to the ganglioside GT1b and perfingolysin O (PFO) that recognizes cholesterol. Each of the above toxin probes were expressed in *E. coli* and purified to homogeneity. To determine which combination of probes is appropriate for each lysosomal storage disease, we performed an evaluation of these probes using a number of patient cell-lines from different lysosomal storage disorders. Some lysosomal storage diseases shared certain staining patterns, suggesting accumulation of similar lipids in their endosomes/lysosomes. The toxins with the most robust signal for the majority of lysosomal storage diseases are the OlyA and VTB probes. Therefore they were used in most studies.

Patient fibroblast cell lines with various lysosomal storage disorders as indicated were obtained from the Coriell Institute for Medical Research. Cells were maintained in the suggested cell culture medium containing 10% fetal calf serum and antibiotics. Cells were grown on glass cover slips in 6-well dishes in complete growth media. Each day, for 3 days, the cells would receive fresh media containing 1 µM test compound or DMSO (control). Cell monolayers were subsequently rinsed with PBS and fixed with phosphate buffered formalin at 4° C. for 30 minutes and permeabilized with 0.1% Triton X-100 in PBS. Cells were incubated with OlyA-GFP, washed and processed for fluorescence microscopy. Images were acquired using the same exposure time for all samples, on a Nikon Eclipse microscope fitted with a charge-coupled-device camera (Nikon, Melville, N.Y.). Fluorescence intensity was determined using the integrated intensity function of MetaVue software; at least 100 cells were quantitated for each.

Staining and quantitation of the glycosphingolipid GL-3 levels: Cells and treatment were as above except that the cells were incubated with VTB-strep-tag followed by incubation with Strep-tactin chromeo 488 (Iba Lifesciences) followed by fluorescence microscopy. Imaging and fluorescence quantitation were as described above.

Alternatively, to quantify the appropriate lipids for each lysosomal storage disease, a toxin ELISA was used. Cells were plated in a 96-well plate at 5000 cells/well. Following treatment with 1 µM test compound for 48 to 72 hours, cells were fixed, permeabilized and probed with the appropriate toxin probe. The amount of bound toxin was quantified using an anti-toxin alkaline phosphatase. Developed plates were read at OD 600 using a Tecan Infinite F200 Pro machine.

Following treatment with the compound of example 50, lysosomal storage materials were decreased as follows: Fabry, 51%; Niemann-Pick type A, 50%; Farber, 48%; Batten's, 59%; Gaucher, 50%; Pompe, 42%; Wolman, 75%; MPS VII, 27%.

Lysosomal storage Disease enzyme assay: The appropriate patient cell line was plated in a 12-well dish. Triplicate wells of cells were treated with 1 µM test compound for 72 hours. Each day the medium was removed and replaced with fresh medium containing test compound. Cells were subsequently lysed in buffer (150 mM NaCl, 50 mM $Na_2HPO_4$, pH 6.9, 1 mM EDTA, 1% Igepal containing protease inhibitor cocktail) and incubated on ice for 30 minutes, after which they were centrifuged at 14k rpm for 10 minutes at 4° C. Lysates were assayed for the disease-specific enzyme activity for 1 hour at 37° C. as follows:

Wolman: Lysosomal acid lipase activity was determined by incubating cell lysate with 1 mM 4-methylumbelliferyl oleate in citrate-phosphate buffer, pH 4.4. Reaction was stopped with 0.1M Tris-HCl, pH 7.6.

Krabbe: β-galactocerebrosidase activity was determined by incubating cell lysate with 0.4 mM 6-hexadecanoy-lamino-4-methylumbelliferyl-β-D-galactoside and 1 mg/mL sodium taurocholate in citrate-phosphate buffer, pH 4.6. Reaction was stopped with 0.4M glycine, pH 10.8.

Batten: Tripeptidyl peptidase II activity was determined by incubating cell lysate with 250 mM Ala-Ala-Phe-7-amido-4-methylcoumarin in citrate-phosphate buffer, pH 4.4. Reaction was stopped with 0.3% trifluoroacetic acid.

Fabry: Galactosidase A activity was determined by mixing lysate with an equal volume of 4 mM 4-methylumbelliferyl α-D-gluco-pyranoside in PBS/0.2 M acetic acid, pH 4.2 (1:1). Reaction was stopped with 1M glycine/1M NaOH, pH 10.

In each case, the fluorescence signal was read in a Tecan Infinite F200 Pro at 360/460 nm excitation/emission pair. In cells from three different patients with Fabry disease (mutation P250T, N34S, N215S), lysosomal a-galactosidase A in cells treated with the compound of example 50 was 122%, 180% and 129% of control, respectively. In cells from patients with Wolman's disease, lysosomal acid lipase activity in cells treated with the compound of example 50 was 180% of control. In cells from patients with Krabbe's disease, β-galactocerebrosidase activity in cells treated with the compound of example 50 was 114% of control. In cells from patients with Batten's disease, peptidase II activity in cells treated with the compound of example 50 was 185% of control.

The ability of compounds of the invention to penetrate the blood-brain barrier (BBB) may be assessed by the following protocol: C57BL6 mice were injected with 30 mg/kg of test compound subcutaneously. Two hours following injection mice were sacrificed and tissues isolated, rinsed with cold saline, dried on filtrate paper, weighed and snap frozen by placing into dry-ice. Samples were stored in 48-well plates (Whatman™ 7701-5500 UNIPLATE™ 48-Well×5 mL Assay Collection & Analysis Microplate, Polypropylene with Rectangular Well & Flat Bottom) at −80° C. until the assay. For the assay, three volumes of water were added to each brain sample and the sample was homogenized using SPEX GenoGrinder. Ten calibration standards (1.0-1000 ng/mL) were prepared in the control blank brain homogenate. Two hundred µL of IS/acetonitrile/MeOH was added to the respective wells of 2-mL 96-well plate and 40 of homogenated tissue samples were pipetted into a respective wells of 2-mL 96-well plate. The plate was capped and vortexed using the pulsing vortex mixer for 5 minutes, then centrifuged for 30 min at 4° C. and 3000 rpm. One hundred fifty µL of supernatant was transferred to a 350-4, Waters 96-well plate using Tecan and 1.0 µL of supernatant was injected into UPLC-MS/MS. In this test, the compound of example 50 was found to exhibit a permeability of 1.058× $10^{-4}$ cm/s. Thus a 30 mg/kg injection of example 50 resulted in a plasma concentration of about 3 µg/mL at one hour and a brain concentration of about 200 ng/mL at one hour. Thus the compound would be expected to be useful in treating lysosomal storage diseases that have a central component, e.g. Niemann-Pick, Batten, Gaucher Type II, Krabbe and mucopolysaccharidosis VII (MPS VII).

The invention claimed is:

1. A method of treating a lysosomal storage disorder comprising administering a compound of formula I

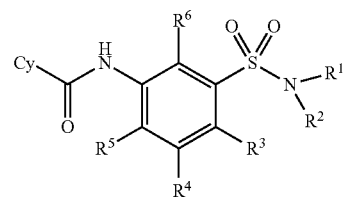

wherein
  $R^1$ is selected from hydrogen and $(C_1-C_6)$alkyl;
  $R^2$ is selected from $(C_1-C_6)$alkyl, optionally substituted benzyl, meta-substituted phenyl and para-substituted phenyl, wherein substituents on the benzyl or phenyl are selected from $(C_1-C_6)$alkyl, halogen, halo$(C_1-C_6)$alkyl, $(C_1-C_6)$alkoxy, and cyano; or
  $R^1$ and $R^2$, together with the nitrogen to which they are attached, form an optionally substituted and/or fused heterocycle;
  $R^3$, $R^4$, $R^5$ and $R^6$ are independently selected from hydrogen, $(C_1-C_6)$alkyl, halogen, hydroxy, cyano, nitro, amino, halo$(C_1-C_6)$alkyl, $(C_1-C_6)$alkoxy, and $(C_1-C_6)$alkoxy substituted with an amine or saturated nitrogen heterocycle;
  Cy is chosen from adamantyl, optionally substituted monocyclic aryl, and optionally substituted monocyclic heteroaryl, with the proviso that when $R^2$ is $(C_1-C_6)$alkyl, Cy is not unsubstituted aryl or heteroaryl.

2. A method according to claim 1 wherein said disorder is chosen from sphingolipidoses and mucopolysaccharidoses.

3. A method according to claim 1 wherein said disorder is chosen from Niemann-Pick C, Niemann-Pick A/B, Fabry Disease, Farber Disease, Wolman Disease, Gaucher's Disease, Krabbe Disease, MPS VII (mucopolysaccharidosis VII), Neuronal Ceroid Lipofuscinosis Type 2 (CLN 2), and Glycogen Storage Type II (Pompe Disease).

4. A method according to claim 1 wherein Cy is an optionally substituted ring selected from optionally substituted pyrazole, pyrrole, thiazole, imidazole, oxazole, pyridine, pyridazine, pyrimidine, thiophene, furan, and phenyl.

5. A method according to claim 4 wherein Cy is a ring selected from substituted pyrrole, ortho-substituted phenyl, meta-substituted phenyl, and optionally substituted pyridine or imidazole, wherein the substituents on the ring are selected from $(C_1-C_7)$hydrocarbon, $(C_1-C_6)$acyl, halo$(C_1-C_6)$alkyl, $(C_1-C_{10})$oxaalkyl and halogen.

6. A method according to claim 1 wherein $R^1$ is selected from hydrogen and $(C_1-C_6)$alkyl.

7. A method according to claim 6 wherein $R^2$ is selected from meta- and para-substituted phenyl.

8. A method according to claim 7 wherein said meta and para substituents are chosen from bromo, chloro, cyano and acetyl.

9. A method according to claim 1 wherein $R^1$ is $(C_1-C_6)$alkyl and $R^2$ is $(C_1-C_6)$alkyl.

10. A method according to claim 1 wherein $R^1$ and $R^2$, together with the nitrogen to which they are attached, form an optionally substituted monocyclic heterocycle.

11. A method according to claim 10 wherein said optionally substituted heterocycle is chosen from pyrrolidine, piperidine, azepine, morpholine and piperazine.

12. A method according to claim 1 wherein $R^1$ and $R^2$, together with the nitrogen to which they are attached, form an optionally substituted fused heterocycle.

13. A method according to claim 12 wherein said optionally substituted fused heterocycle is chosen from tetrahydrobenzoazepine, tetrahydroquinoline, tetrahydroisoquinoline, indoline and isoindoline.

14. A method according to claim 1 wherein $R^3$ is selected from hydrogen, $(C_1-C_6)$alkyl, halogen, hydroxy, cyano, nitro, amino, halo$(C_1-C_6)$alkyl, $(C_1-C_6)$alkoxy, and $(C_1-C_6)$alkoxy substituted with an amine or saturated nitrogen heterocycle; and $R^4$, $R^5$ and $R^6$ are independently selected from hydrogen and fluorine.

15. A method according to claim 14 wherein $R^3$ is selected from hydrogen, methyl, ethyl, methoxy, dimethylaminopropoxy, and hydroxy; $R^4$ and $R^6$ are hydrogen; and $R^5$ is hydrogen or fluorine.

16. A compound of formula:

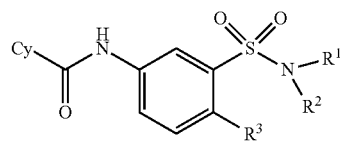

wherein:
(A) Cy is a substituted pyridine, wherein the substituents on the pyridine are $(C_1-C_7)$hydrocarbon, $(C_1-C_6)$acyl, halo$(C_1-C_6)$alkyl, or $(C_1-C_{10})$oxaalkyl;
$R^1$ is hydrogen;
$R^2$ is para-substituted phenyl, wherein the substituents on the phenyl are selected from $(C_1-C_6)$alkyl, halogen, halo$(C_1-C_6)$alkyl, $(C_1-C_6)$alkoxy, and cyano, provided that a para substituent on the phenyl is bromo; and
$R^3$ is cyano, halo$(C_1-C_6)$alkyl, $(C_1-C_6)$alkoxy, or $(C_1-C_6)$alkoxy substituted with an amine or saturated nitrogen heterocycle;
or
(B) Cy is an optionally substituted imidazole, wherein the substituents on the imidazole ring are independently selected from $(C_1-C_7)$hydrocarbon, $(C_1-C_6)$acyl, halo $(C_1-C_6)$alkyl, $(C_1-C_{10})$oxaalkyl and halogen
$R^1$ is selected from hydrogen and $(C_1-C_6)$alkyl;
$R^2$ is selected from optionally substituted $(C_1-C_6)$alkyl, benzyl, meta-substituted phenyl and para-substituted phenyl, wherein substituents on the benzyl or phenyl are selected from $(C_1-C_6)$alkyl, halogen, halo$(C_1-C_6)$alkyl, $(C_1-C_6)$alkoxy, and cyano; and
$R^3$ is selected from $(C_1-C_6)$alkyl, halogen, hydroxyl, cyano, amino, halo$(C_1-C_6)$alkyl, $(C_1-C_6)$alkoxy, and $(C_1-C_6)$alkoxy substituted with an amine or saturated nitrogen heterocycle;
or
(C) Cy is an optionally substituted imidazole, wherein the substituents on the imidazole ring are independently selected from $(C_1-C_2)$alkyl, $(C_1-C_6)$acyl, halo$(C_1-C_6)$alkyl, $(C_1-C_{10})$oxaalkyl and halogen;
$R^1$ and $R^2$, together with the nitrogen to which they are attached, form an optionally substituted and/or fused heterocycle; and
$R^3$ is selected from $(C_1-C_6)$alkyl, halogen, hydroxyl, cyano, amino, halo$(C_1-C_6)$alkyl, $(C_1-C_6)$alkoxy, and $(C_1-C_6)$alkoxy substituted with an amine or saturated nitrogen heterocycle.

17. A compound according to claim 16 wherein $R^3$ is methoxy or ethyl.

18. A compound according to claim 16 wherein Cy is unsubstituted imidazolyl.

19. A compound according to claim 16 wherein Cy is substituted imidazole.

20. A compound according to claim 19 wherein Cy is an imidazole substituted with a substituent selected from trifluoromethyl, chloro, methyl, and ethyl.

21. A compound according to claim 16 wherein Cy is substituted or unsubstituted imidazole; $R^1$ is hydrogen; and $R^2$ is para-substituted phenyl, wherein the substituents on the phenyl are selected from $(C_1-C_6)$alkyl, halogen, halo$(C_1-C_6)$alkyl, $(C_1-C_6)$alkoxy, and cyano, provided that the para substituent on the phenyl is bromo.

22. A compound according to claim 16 wherein Cy is an optionally substituted imidazole and $R^1$ and $R^2$, together with the nitrogen to which they are attached, form an optionally substituted and/or fused heterocycle.

23. A compound of formula:

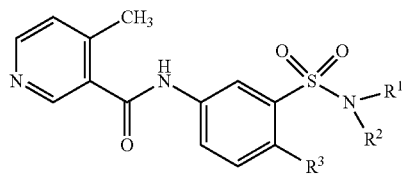

wherein:
$R^1$ is selected from hydrogen and $(C_1-C_6)$alkyl;
$R^2$ is selected from optionally substituted $(C_1-C_6)$alkyl, benzyl, meta-substituted phenyl and para-substituted phenyl, wherein substituents on the benzyl or phenyl are selected from $(C_1-C_6)$alkyl, halogen, halo$(C_1-C_6)$alkyl, $(C_1-C_6)$alkoxy, and cyano; or
$R^1$ and $R^2$, together with the nitrogen to which they are attached, form an optionally substituted and/or fused heterocycle;
$R^3$ is selected from $(C_1-C_6)$alkyl, halogen, hydroxyl, cyano, amino, halo$(C_1-C_6)$alkyl, $(C_1-C_6)$alkoxy, and $(C_1-C_6)$alkoxy substituted with an amine or saturated nitrogen heterocycle.

24. A compound according to claim 23 wherein $R^3$ is methoxy or ethyl.

25. A compound according to claim 24 wherein $R^1$ is hydrogen; and
$R^2$ is para-substituted phenyl, wherein the substituents on the phenyl are selected from $(C_1-C_6)$alkyl, halogen, halo$(C_1-C_6)$alkyl, $(C_1-C_6)$alkoxy, and cyano, provided that the para substituent on the phenyl is bromo.

26. A compound according to claim 16 wherein Cy is chosen from 4-methylpyridin-3-yl, imidazole-4-yl, and 2-phenylimidazole-4-yl.

27. A compound according to claim 16 of formula
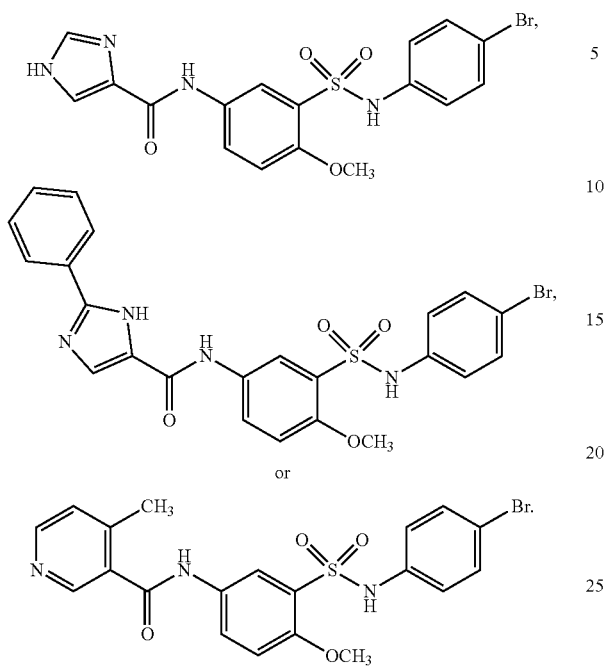
28. A pharmaceutical composition comprising a pharmaceutically acceptable carrier and a compound according to claim 16.
* * * * *